United States Patent [19]

Alfano et al.

[11] Patent Number: 5,034,903
[45] Date of Patent: Jul. 23, 1991

[54] APPARATUS AND METHOD FOR MEASURING THE TIME EVOLUTION OF CARRIERS PROPOGATING WITHIN SUBMICRON AND MICRON ELECTRONIC DEVICES

[76] Inventors: Robert R. Alfano, 3777 Independence Ave., Bronx, N.Y. 10463; Ping-Pei Ho, 240-42 69th Ave., Douglaston, N.Y. 11362

[21] Appl. No.: 303,195
[22] Filed: Jan. 30, 1989
[51] Int. Cl.$^5$ ............................................. G01N 23/225
[52] U.S. Cl. ............................... 364/569; 324/158 R; 250/311
[58] Field of Search ................... 364/569; 324/158 D, 324/158 R, 96; 250/492.2, 310, 311, 213 VT; 356/368, 71-73

[56] References Cited

U.S. PATENT DOCUMENTS

| | | | |
|---|---|---|---|
| 4,327,285 | 4/1982 | Bradley | 250/213 VT |
| 4,482,863 | 11/1984 | Auston et al. | 324/158 D |
| 4,721,910 | 1/1988 | Boker et al. | 324/158 R |
| 4,764,674 | 8/1988 | Kinoshita | 250/310 |
| 4,777,523 | 10/1988 | Yokoto et al. | 250/311 |
| 4,829,240 | 5/1989 | Kitaoka | 324/158 R |
| 4,845,425 | 7/1989 | Beha et al. | 324/158 R |
| 4,851,767 | 7/1989 | Halbout et al. | 324/158 R |
| 4,855,591 | 8/1989 | Nakamura et al. | 356/368 |
| 4,866,273 | 9/1989 | Kobayashi et al. | 250/310 |
| 4,902,963 | 2/1990 | Brust | 324/158 R |

Primary Examiner—Parshotam S. Lall
Assistant Examiner—Michael Zamelli
Attorney, Agent, or Firm—Irving M. Kriegsman

[57] ABSTRACT

An apparatus for determining and displaying the time evolution profile of electron carriers present within a submicron or micron device comprises a laser for generating a beam of ultrafast pulses of ultraviolet light. A first beam splitter splits each pulse into a transmitted beam and a reflected beam. The transmitted beam travels through a time delay circuit, and is then converted into a train of ultrafast electrical pulses which are transmitted to the device. The reflected beam is focused on the device. An electron detector, also focused on the device, collects the ejected electrons resulting from the interaction of the light pulse and electrical pulse to produce an electrical signal. The signal is then magnified in intensity by an amplifier and directed at a cathode ray tube to cause an image to appear thereon. A SIT vidicon camera converts the image into an electrical signal and transmits the signal to a computer. The computer generates a time evolution profile from the signal received which is sent to a monitor for display.

15 Claims, 3 Drawing Sheets

T = 10 PS

T = 7.5 PS

T = 5 PS

T = 2.5 PS

T = 0 PS

APPARATUS AND METHOD FOR MEASURING THE TIME EVOLUTION OF CARRIERS PROPOGATING WITHIN SUBMICRON AND MICRON ELECTRONIC DEVICES

BACKGROUND OF THE INVENTION

The present invention relates to an apparatus and method for measuring the time evolution of carriers (electrons and holes) propagating within submicron and micron electronic devices.

Electronic devices used in computers and communication systems are continually becoming both smaller in physical size and faster in execution capabilities. With technology progressing at its present rate, it is not inconceivable that submicron and micron sized electronic devices will soon become commonplace in the computer and communications industries. While submicron and micron sized electronic devices bring innumerable benefits to these industries, their extremely small size creates problems with regard to testing. For one thing, the size of submicron electronic device makes it virtually impossible using conventional state-of-the-art technology to observe directly the ultrafast (frequently in the picosecond and femtosecond regimes) kinetic activity and pathways of carriers present within such a device. This is because the current technology uses light to probe the spatial distribution of the carriers and light is limited in resolution to a few microns. Nonetheless, despite present day technological inadequacies, there persists a definite need to know the speed and pathways of carriers propogating in submicron and micron electronic devices.

In the past, electron microscope have frequently been used to explore spatial relationships in the submicron and micron world.

Electron microscopes are traditionally classified as either transmission or scanning instruments.

In a transmission electron microscope an electron beam, which is generated by an electron gun, is focused by a magnetically operated condenser lens onto the specimen. The specimen is usually mounted in a mechanical stage, which forms a part of a magnetically operated objective lens. The objective lens forms an intermediate image of some 50 to 100 times magnification of the specimen in the vicinity of a magnetically operated projector lens, which further magnifies the image and projects the magnified image onto an observation screen for viewing.

In a scanning electron microscope, which is very similar in operation and construction to a closed circuit television system, a finely focused electron beam is formed by an electron lens system. The beam sweeps rapidly across the specimen, stimulating the emission of secondary electrons from the area it strikes. The secondary electrons are then collected to produce a signal which is then amplified. The amplified signal is then used to vary the intensity of a second electron beam as it scans a cathode ray tube in synchronism with the first beam to produce a light image of the specimen.

One drawback to the use of electron microscopes is that, when used in the manner described above, they lack the independent capability to temporally resolve ultrafast events. This makes electron microscopes, when used alone, unsuitable for measuring and recording the ultrafast time evolution of carriers within submicron and micron electronic devices.

Streak cameras, are a well known type of instrument which have been used to directly measure the time dynamics of luminous events. A typical streak camera includes an entrance slit which is usually rectangular, a streak camera tube, input relay optics for imaging the entrance slit onto the streak camera tube, sweep generating electronics, and output relay optics for imaging the streak camera image formed at the output end of the streak camera tube onto an external focal plane. The image at the external focal plane is then photographed by either a conventional still camera or a television camera. The streak camera tube generally includes a photocathode, an accelerating mesh, sweeping electrodes, and a phosphor screen. The streak camera tube may also include a microchannel plate. In the operation of a streak camera, light incident on the photocathode is converted into a streak image, which is formed on the phosphor screen with the intensity of the streak image from the start of the streak to the end of the streak corresponding to the intensity of the light incident thereon during the time window of the streak. The time during which the electrons are swept to form the streak image is controlled by the sweep electronics which supplies a very fast sweep signal to the sweeping electrodes. The input optics of the streak camera may comprise a single lens or a plurality of lenses.

SUMMARY OF THE INVENTION

An apparatus for measuring the ultrafast time evolution profile of carriers propogating within a submicron or micron sized electronic device which is constructed according to the teachings of the present invention comprises in one embodiment means for generating a train of ultrafast pulses of ultraviolet light, means for splitting the train of pulses into two trains of pulses, one traveling along a first beam path and the other traveling along a second beam path, the train of pulses in the second beam path striking the device, means for receiving the train of pulses traveling along the first beam path and generating a train of ultrafast electrical pulses, means for transmitting said ultrafast electrical pulses to the device, variable time delay means for incrementally changing the arrival time between the light pulses and the electrical pulses so that the interaction of the light pulses and the electrical pulses can be measured at different locations within the device, electron microscope means for creating images of electrons ejected by the device, camera means for converting the images formed by the electron microscope means into electrical image signals, computer means for processing and/or storing said electrical image signals and display means for displaying the electrical signals.

The method of the invention using the above apparatus involves propogating a series of ultrafast electrical pulses through a submicron or micron device to be tested, simultaneously illuminating the device with ultrashort ultraviolet light pulses, varying the arrival time of the electrical pulses relative to the light pulses so that the electrical and light pulses intersect at different locations in the device and then recording processing and displaying information corresponding to electrons emitted from the device.

An apparatus for determining and displaying the ultrafast time evolution profile of carriers propogating within a submicron or micron electronic device which is constructed according to the teachings of another embodiment of the present invention comprises means for generating a continuous wave or long pulse of ultraviolet light, means for splitting the light into two beams, one traveling along a first beam path and the other traveling along a second beam path, the beam of light in the second beam path striking the device, means for receiving the beam of light traveling along the first beam path and generating an ultrafast electrical pulse, means for transmitting the ultrafast electrical pulse to the device, streak camera means for creating an image of electrons ejected by the device as said electrical pulse propogates through the device from one end to the other, means for converting the images formed by the streak camera means into electrical signals, means for processing and storing the electrical signals and means for displaying the electrical signals.

The method according to this second embodiment of the invention comprises propogating an ultrashort electrical pulse through the device, illuminating the device with a continuous wave or long pulse of light as said electrical pulse moves from one end of the device to the other, forming a streak image of electrons emitted from the device as a result of the interaction of the light pulse and the electrical pulse, and then recording, processing, storing and displaying the streak image.

It is an object of the present invention to provide an apparatus for determining and displaying the time evolution profile of carriers propogating within a submicron or micron electronic device.

It is another object of the present invention to provide an apparatus as described above which utilizes electron optics.

It is still another object of the present invention to provide an apparatus as described above which can be adjusted to reduce noise.

It is a further object of this invention to provide a method of measuring the time evolution of carriers propogating in a submicron or micron electronic device.

Various features and objects will appear from the description to follow. In the description, reference is made to the accompanying drawings which form a part thereof, and in which is shown by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

The present invention is directed to a technique for observing the time evolution of carriers propogating within submicron and micron electronic devices. The technique utilizes electron optics for imaging, UV picosecond and femtosecond pulses for pumping and ultrafast electrical pulses. In one version of the invention an electron microscope with the electron source removed is employed to form an image of electrons ejected from the device while in another version of the invention a streak camera in which the photocathode is replaced with the device to be examined is employed to form an image of electrons ejected from the device.

Submicron and micron electronic devices, such as for example field effect transistors (FET's), are rapidly gaining widespread use in the computer and communications industries. Having knowledge of the time evolution of carriers within such a device is essential to understanding how fast and through what pathways electrical current flows through the device. Until now, however, the infinitesimal size of these devices has made it impossible for one to obtain this direct information. The biggest obstacle has been that submicron devices could not be observed through light microscopes or other instruments using light as a probe because light has a wavelength range of approximately 3000 to 7500 Angstroms and therefore cannot be used to resolve objects less than this size. However, in contrast with light, electrons have a wavelength of approximately 0.05 Angstroms. Therefore, instruments using electrons as a probe are capable of resolving objects as small as about a nanometer.

Generally speaking, the present invention, according to one embodiment, uses the increased sensitivity of electron measuring devices to observe the propagation of a train of ultrafast test electrical pulse through a submicron or micron sized electronic device. The underlying theory is as follows. When a pulse of light of appropriate wavelength strikes such an electronic device (of photoemissive material) some electrons will be ejected from the conduction, valence or fermi levels to the vacuum state. If an electrical pulse propogates through the device at the same time, the number of electrons emitted will be increased when the light pulse an electrical pulse intersect in time on the device. When the electrons are ejected from the device they can be detected by a suitable electron-sensitive measuring device. By delaying the arrival time between each light pulse and its associated electrical pulse by different amounts, the transport of the carriers at different locations in the device can be measured and a profile showing the time evolution of carriers propogating within the device can be obtained.

Figure 1:
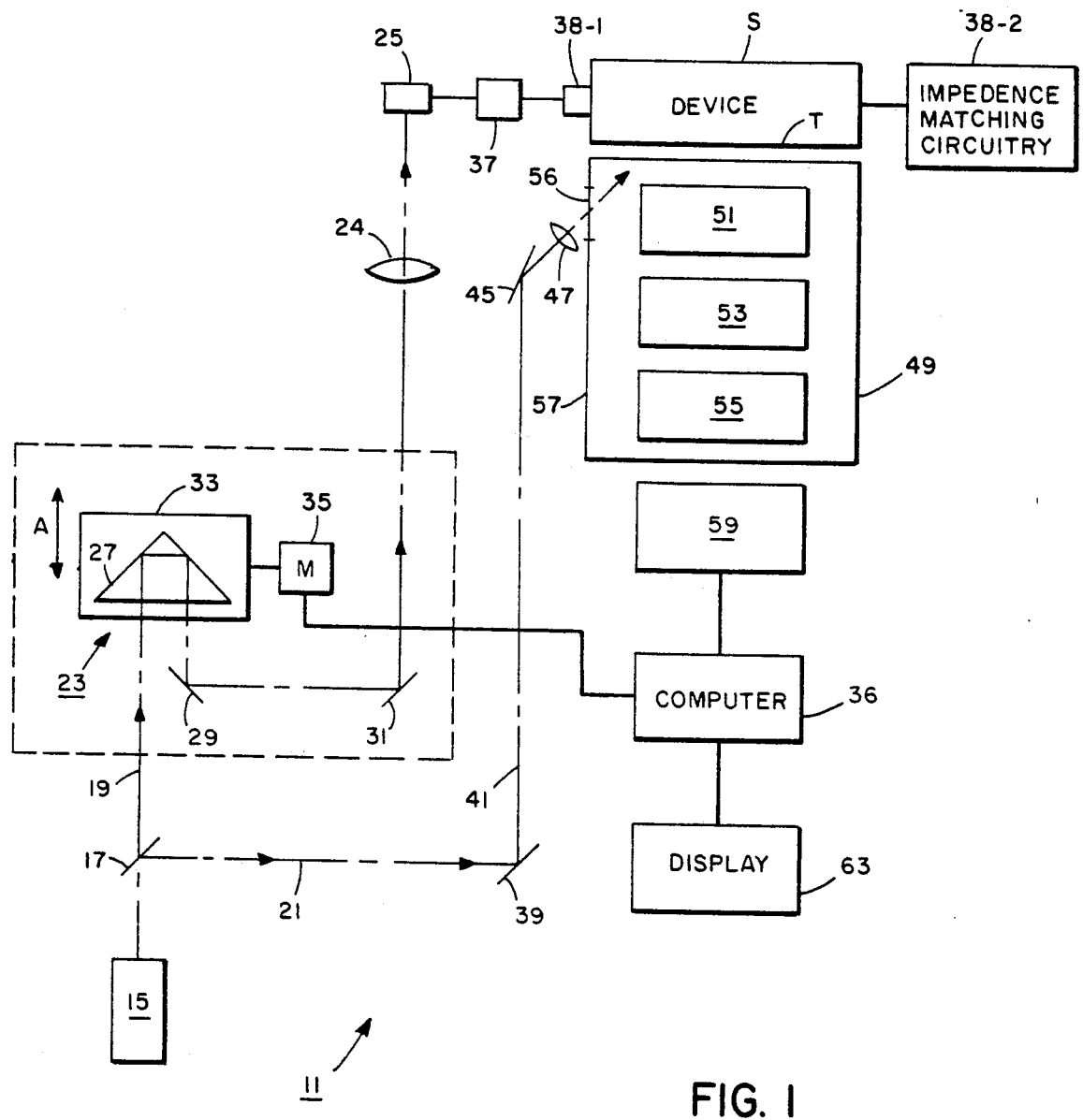
FIG. 1 is a schematic diagram of an apparatus using a modified electron microscope for measuring the ultrafast time evolution of carriers within a submicron or micron electronic device.
Figure 2E:
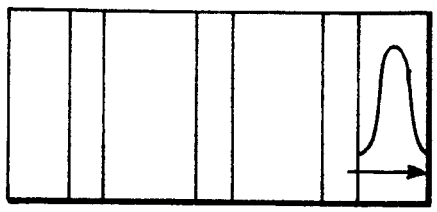
FIGS. 2(a) through 2(e) are schematic representations showing the location of an electrical pulse at different times as it propogates within one micron sized electronic device; and, FIG. 3 is a schematic diagram of an apparatus using a modified streak camera for measuring the ultrafast time evolution of carriers within a submicron or micron electronic device.
Figure 2D:
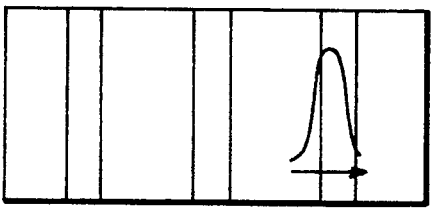
Figure 2C:
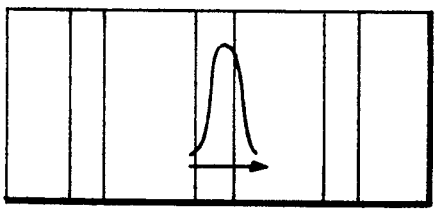
Figure 2B:
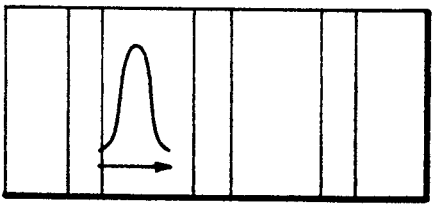
Figure 2A:
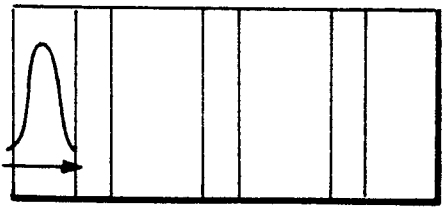

Referring now to the drawings and more particularly to FIG. 1, there is illustrated an apparatus for determining and displaying the time evolution profile of carriers within a submicron or micron electronic device according to this invention, the apparatus being represented generally by reference numeral 11.

Apparatus 11 comprises a laser 15 which produces a train of UV picosecond or femtosecond pulses of light and a beamsplitter 17. Laser 15 may comprise a mode locked UV laser or a visible mode locked laser with harmonic generators. Examples are a CPM mode locked laser, a dye, YAG or glass mode locked laser or an excimer laser. To minimize noise, the particular laser selected is one wherein the wavelength of the light emitted is no greater than the amount of energy needed to move electrons within submicron device S from the conduction band to the vacuum level (typically about 2.5 ev to 4.0 ev). Light emitted from laser 15 is split by beamsplitter 17 into two beams, namely, a transmitted beam traveling along beam path beam 19 and a reflected beam traveling along a beam path 21. As will be described more fully below, the transmitted beam is used to trigger the transmission of ultrafast electrical pulses to the device S being examined while the reflected beam is used to illuminate device S.

A variable time delay device 23 is disposed along the path of transmitted beam 19 for selectively varying the path length of the transmitted beam. The output of variable time delay device 23 is focused by a lens 24 onto a PIN photodiode 25 which serves as a trigger device. Instead of a PIN photodiode, a photoconductive switch may be employed.

As can be seen, time delay device 23 comprises a prism 27 and a pair of mirrors 29 and 31. Prism 27 is mounted on a support 33 assembly which is selectively movable in the direction indicated by arrow A by a motor 35 which receives instructions from a computer 36. Delay device 23 can be displaced by distances that translate into incremental time differences of one or two picoseconds or femtoseconds. As can be seen, light from laser system 15 is reflected off of prism 27 is reflected off mirrors 29 and 31 and then brought to focus by lens 24 on PIN photodiode 25

On striking PIN photodiode 25, the light pulse is converted into an electrical trigger signal which is fed through a line 36 into a variable pulse generator 37. The output of pulse generator 37 is an ultrafast (typically, about 1 picosecond) electrical pulse. A cable 38 connected at one end to pulse generator 37 and at the other end through an SMA connector to one end of device S is used to transmit electrical pulse output from pulse generator 37 to device S. Matching impedance circuitry 38-2 is at the other end of device S.

Instead of using a variable pulse generator, the output of the PIN photodiode (or the photoconducting switch) may be electrically coupled directly to the submicron devices. One advantage of using a pulse generator is that the electrical pulse sent to submicron device S may be varied, if desired, in terms of duration and intensity.

The reflected beam travelling along path 21 is deflected off a mirror 39, a mirror 45 and focused by a lens 47 onto the (entire) top surface T of device S, the beam uniformly illuminating the entire device S.

An electron microscope 49 is also focused on the entire top surface T of device S and creates an image representing the number of electrons ejected from device S as a result of the interaction of the light pulse and the corresponding electrical pulse and the loci of their ejection. In its simplest construction, microscope 49 may consist of a scanning type electron microscope in which the electron source has been removed. Thus, microscope 49 includes an electron detector 51, a signal amplifier 53 and a cathode ray tube. Also, a window 56 is formed in the housing 57 of election microscope 49 to allow light traveling along path 41 to reach submicron device S. Electron detector 51 collects the electrons ejected from device S to produce an electrical signal. Signal amplifier 53 magnifies the electrical signal and directs the signal to cathode ray tube 55. When the electrons impinge on tube 55, a light image is formed.

A silicon intensified target (SIT) or a CCD vidicon camera 59 or other similar instrument is focused on cathode ray tube 55 and converts the light images displayed on tube 55 into electrical signals. Computer 36, which is electrically connected to SIT camera 59, receives the electrical signal output of SIT camera 59 for processing and storage. The information so obtained and processed is displayed on a monitor 63.

In the operation of apparatus 11, a train of UV pulses are emitted from laser 15. As can be appreciated, for any particular position of prism 27, the intersection of the light an electrical pulses will occur at some particular location on device S. As can also be appreciated, by moving prism 27 this location of the interaction between the electrical and light pulses can be changed. Moving prism 27 away from laser system 13 will increase the path length from laser 15 to trigger 25 and will cause the electrical pulses from generator 37 to arrive at device S at a later time and thus migrate a shorter distance across device S before they interact with their corresponding light pulses. Thus, by appropriately changing the path length, measurements can be obtained of electrons emitted at different locations throughout device S. FIG. 2 shows the location of an electrical pulse in device S at five different time intervals, with T=0 representing no delay, T=1 representing a delay of 1 picosecond, T=2 a delay of 2 picoseconds and so forth. As is known, in one picosecond a carrier travelling $10^7$ cm/sec will travel a distance of 0.1 microns and in ten picoseconds will travel a distance of one micron.

The electrons ejected by device S on the interaction of each electrical pulse and its associated light pulse are detected by electron microscope 49, recorded by camera 59, stored and processed in computer 36 and then displayed on monitor 63.

Figure 3:
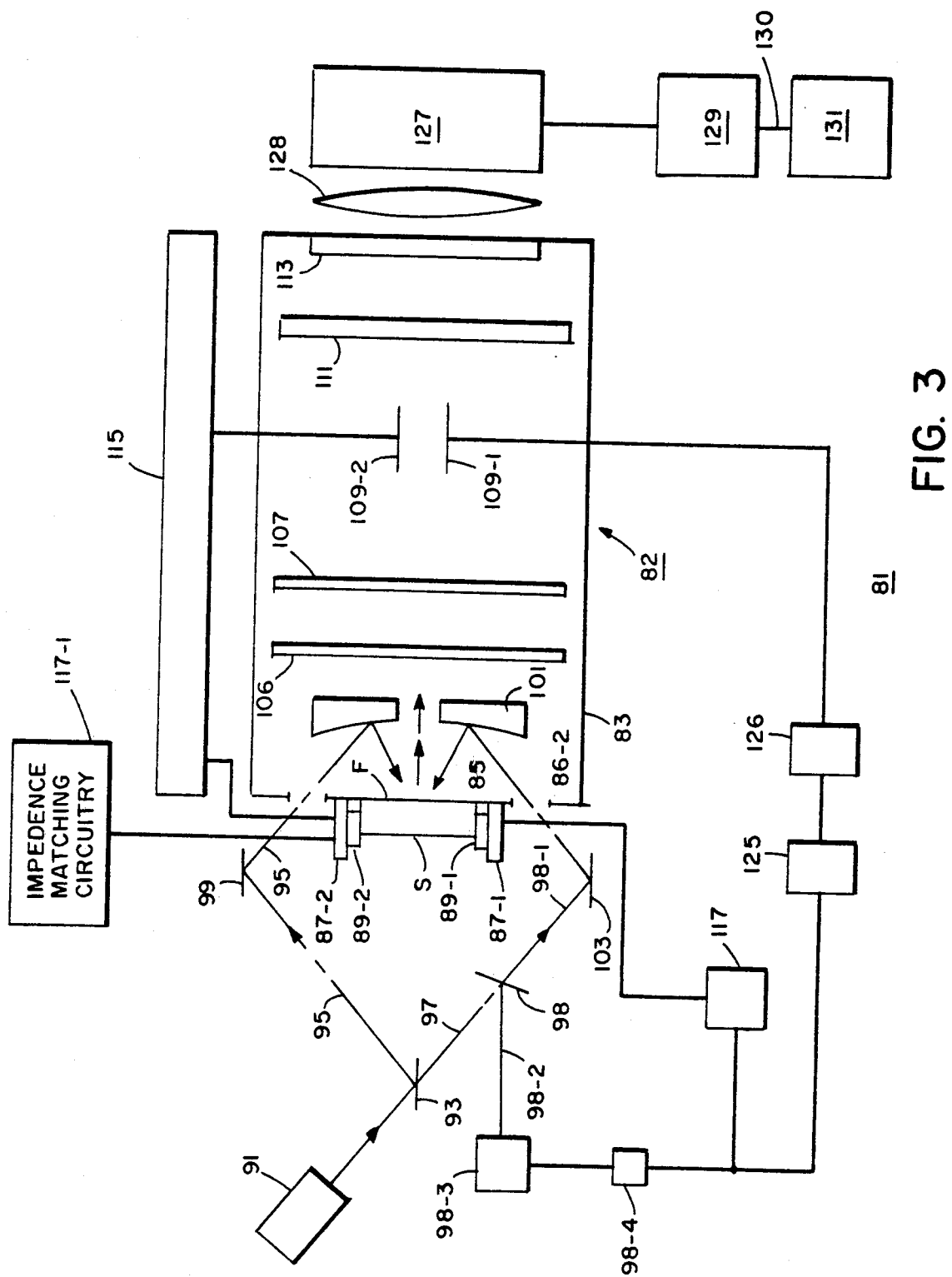

Referring now to FIG. 3, there is illustrated another embodiment of an apparatus for determining and displaying a time evolution profile of the electron carriers present within a submicron device S, the device being represented generally by reference numeral 81. Device S has a front surface F and a back surface B.

Apparatus 81 comprises a streak camera 82. Camera 82 includes a streak camera tube 83 in which the photocathode has been removed and which includes an opening 85 at the front instead of a slit and a pair of light receiving windows 86-1 and 86-2, also at the front. A pair of brackets 87-1 and 87-2 for holding a device S to be examined are fixedly mounted, by means not shown, on tube 83 in front of opening 85. Device S is removably mounted on brackets 87. Subminiature coaxial to strip line microwave launchers 89-1 and 89-2 are fixedly mounted on clamps 87-1 and 87-2, respectively and are in electrical contact with device S. Preferably, device S is mounted on brackets 87-1 and 87-2 such that the front surface F of device S lies flush with opening 85.

Apparatus 81 also includes a laser system 91, which outputs a beam of ultraviolet light. The beam may either be a continuous wave or long pulses (i.e. pulses larger than one nanosecond). Laser system 91 may comprise a continuous wave UV laser, such as an excimer laser or a YAG laser with hamonic generators or a dye laser with harmonic generators. A beam splitter 93 is disposed along the path of light emitted by laser system 91 to split the light emitted therefrom into a reflected beam 95 and a transmitted beam 97. Reflected beam 95 is reflected off a mirror 99 and directed through window 86-1 into tube 83. After passing through window 86-1, beam 95 is focused by a concave annularly shaped mirror 101 onto the entire front surface F of submicron device S. Transmitted beam 97 strikes a beam splitter 98. The transmitted beam 98-1 from beamsplitter 98 is reflected off a mirror 103 and directed through opening 86-2. After passing through opening 86-2, beam 98-1 is focused by mirror 101 onto the inner surface of device S. Preferably, beams 95 and 98-1 impinge on device S at similar angles so that device S is irradiated uniformly. The reflected beam 98-2 from beamsplitter 98 is passed through a variable time delay 98-3 and strikes a PIN photodiode 98-4. Instead of a PIN photodiode, a photoconductive switch may be employed.

Also disposed within tube 83 behind focusing mirror 101 are a spatial filter 106, an accelerating mesh 107, sweep electrodes 109-1 and 109-2, a microchannel plate 111 and a phosphor screen 113. A high DC bias voltage source and a voltage divider circuit shown collectively as a box 115 is outside tube 83. As can be seen, streak camera tube 83 is similar to a conventional streak camera tube except that the photocathode has been removed, a focusing mirror 101 has been provided inside tube 83 added, windows have been formed to allow light to strike the front surface F of device S, the input slit has been replaced by an opening corresponding in size to device S and a mounting structure for holding a device S to be examined is provided in front of the tube.

The electrical signal output from PIN photodiode 98-4 is fed into an ultrafast electrical pulse generator 117 which outputs an ultrafast voltage pulse (typically about 1 picosecond). The ultrafast voltage pulse is applied to launcher 89-1. Impedence matching circuitry 117-1 is connected to launcher 89-2. PIN photodiode 98-4 also provides a trigger pulse which is coupled through a delay 125 to a sweep voltage generator 126 which is coupled sweep electrode 109-1.

A video camera 127 such as a silicon intensified target (SIT) vidicon or a CCD vidicon is focused by a lens 128 on phosphor screen 113. Camera 127 converts the streak image displayed on screen 113 into electrical signals. The signals are sent to a computer 129 over line 130, which processes and/or analyzes the signals to generate a time evolution profile of the electron carriers present within submicron device S. The profile information may then be sent to a monitor 131 for display.

Apparatus 81 operates in the following manner: Laser system 91 is activated, causing beams 95 and 98-1 to continuously illuminate the inner surface of device S. At the same time, pulse generator 117 is triggered, causing picosecond voltage pulses to be emitted therefrom. The ultrafast voltage pulses are transmitted to device S through cable 119 and launcher 89-1 and then propagate across device S in the direction of launcher 89-2. Because device S is continuously illuminated (or at least for a duration much greater than that of the electrical pulse and much greater than the time for the electrical pulse to travel across device S), electrons will be ejected from submicron device S as each pulse travels along device S from one end to the other. At a time Ti, the electrical pulse is located inside device S. The electrons, ejected from device S at time Ti, are conducted through tube 83 in the direction of phosphor screen 113. Because of the synchronization provided by time delay 126, as the electrons pass between electrodes 109-1 and 109-2, their respective trajectories are angularly deflected as a function of time. After being temporally resolved by electrodes 109, the electrons proceed to travel through tube 83 until they impinge on phosphor screen 113, creating a streak image of the pulse at time Ti as it travels across device S over a time window which may be, for example, 100 picoseconds. The streak image is converted into electrical signals by camera 127 and transmitted to computer 129. Computer 129 analyzes the signals and generates therefrom a time evolution profile of the carriers present within submicron device S. The profile may then be transmitted to monitor 131 for display. As an example, assume the light is incident on device S over a time window of 0 to 100 picoseconds. The electrical pulse will enter device S at 50 picoseconds and travel across device S in about 10 picoseconds. The light imaged on the phosphor screen will be from the 50 to 60 picosecond time period. Using the length of the 10 picosecond sweep, one can then calculate the velocity of the carriers through device S.

It should be understood that the invention may also be used, if desired, in examining electronic devices larger than submicron in size.

The embodiments of the present invention are intended to be merely exemplary and those skilled in the art shall be able to make numerous variations and modifications to it without departing from the spirit of the present invention. All such variations and modifications are intended to be within the scope of the present inventions as defined by the appended claims.

What is claimed is:

1. Apparatus for measuring the time evolution profile of electron carriers present within an electronic device, the electronic device having a front surface and a rear surface and a size of about a micron or less, the apparatus comprising:
   a) means for generating a beam of pulses of light, said pulses of light being in the order of picoseconds or less;
   b) means for splitting said beam into first and second beams;
   c) means for focusing said second beam onto the entire front surface of the device;
   d) means for receiving said first beam and outputting a train of electrical pulses said electrical pulses being on the order of about a picosecond;
   e) means for transmitting said electrical pulses to the device;
   f) impedence matching circuitry attached to said device;
   g) time delay means interposed along the path of said first beam for selectively changing the path length traveled by said first beam so that the light pulses and electrical pulses can be made to intersect at different locations on the electronic device; and
   h) electron microscope means focused on the front surface of the device for creating images representing the number and origin of electrons ejected by the device.

2. The apparatus of claim 1 and furthe including means focused on the imaging means for converting the images into electrical signals.

3. The apparatus of claim 2 and further including means for processing said electrical signals to generate a time evolution profile of the carriers within the device.

4. The apparatus of claim 3 and further including means for displaying the time evolution profile produced by said processing means.

5. The apparatus as recited in claim 1 wherein said electron microscope means focused on the device for creating images representing the number and origin of electrons ejected by the device comprises an electron detector for collecting the ejected electrons to produce an electrical signal, an amplifier connected to said electron detector for magnifying the intensity of the electrical signal, and a cathode ray tube for displaying a light image proportional in intensity to the intensity of the electrical signal.

6. The apparatus as recited in claim 5 wherein said means for producing a train of electrical pulses comprises a PIN photodiode.

7. The apparatus as recited in claim 5 wherein said means for producing an electrical signal comprises a photoconductive switch.

8. Apparatus for determining and displaying a time evolution profile of electron carriers present within a device that is micron sized or less, the device having a front surface and a back surface, the apparatus comprising:
   a) a streak camera tube having a front and a back, an opening in the front and having disposed therein spatial filtering means, an accelerating mesh, a pair of sweeping electrodes, a microchannel plate, a phosphor screen, and bias voltage means;
   b) means for removably mounting the device in the opening at the front of the streak camera tube with the front surface of the device facing into said streak camera tube;
   c) means electrically connected to the device for producing an electrical pulse which is transmitted through the device, said pulse being on the order of about a picosecond;
   d) means for irradiating the entire front surface of the device with a pulse of light, said pulse of light being on the order of picoseconds or less;
   e) whereby, electrons are ejected from the front surface of the device into the streak camera tube in the direction of said phosphor screen when the light pulse and the electrical pulse overlap spatially and temporally on the device;
   f) means for synchronizing the activation of said sweep electrodes with the arrival of the ejected electrons thereat;
   g) whereby the ejected electrons, before impinging on said phosphor screen, are angularly deflected by the sweeping electrodes as a function of time so as to create a streak image on the phosphor screen;
   h) means focused on the phosphor screen for converting the streak image into an electrical signal;
   i) means electrically coupled to said converting means for processing said electrical signal to generate a time evolution profile of the electron carriers within the device; and
   j) means for displaying said time evolution profile.

9. Apparatus as recited in claim 8 wherein said means for removably mounting said device in front of the streak camera tube comprises a pair of brackets and wherein said apparatus further includes first and second microwave launchers, each microwave launcher being mounted on one of the brackets.

10. Apparatus as recited in claim 9 wherein said means for irradiating the inner surface of said device comprises a continuous wave ultraviolet laser.

11. A method for measuring the time evolution profile of electron carriers present within a submicron or micron electronic device, the method comprising:
   a) generating a beam of pulses of light;
   b) splitting said beam into first and second beams;
   c) focusing said second beam onto the device;
   d) receiving said first beam and outputting a train of electrical pulses;
   e) transmitting said electrical pulses through the device;
   f) selectively changing the path length traveled by said first beam so that the light pulses and electrical pulses intersect at different locations on the electronic device, and
   g) creating images representing the number and origin of electrons ejected by the device on overlapping of said light pulses and said electrical pulses.

12. A method of measuring the time evolution of carriers within an electronic device, the electronic device having a front surface and a rear surface, the method comprising:
   a. illuminating the entire front surface of the electronic device with a beam of light,
   b. simultaneously therewith propagating an electrical pulse through the electronic device,
   c. forming a streak image of electrons emitted from the front surface of the device as the electrical pulse propogates through the device, and then
   d. processing the streak image.

13. The apparatus as recited in claim 5 wherein said means for producing an electrical signal comprises a microchannel plate photodetector.

14. Apparatus for measuring the time evolution of carriers propogating within an electrical device, the electrical device having a front surface, a back surface and a pair of ends, the apparatus comprising:
   a. means for producing a beam of pulses of light;
   b. means for splitting the beam of pulses of light into two beam parts;
   c. means for illuminating the entire front surface with one of said beam parts;
   d. means for converting the other beam part into a train of electrical pulses;
   e. means for transmitting said train of electrical pulses through the electrical device from one end to the other;
   f. electron microscrope means for producing images representing the number and origin of electrons ejected by the device on overlapping of said light pulses and electrical pulses;
   g. means for converting the images into electrical signals,
   h. computer means for processing said electrical signals; and
   i. display means for displaying the processed electrical signals.

15. Apparatus for producing a time evolution profile of electron carriers present within an electrical device, the electrical device having a front surface and a back surface, the apparatus comprising:
   a. means for generating a beam of light pulses;
   b. means for splitting the beam of light pulses into first and second beam parts;
   c. means for converting said second beam part into a train of electrical pulses;
   d. a streak camera tube having therein an accellerating mesh, sweeping electrodes and a phosphor screen;
   e. means for mounting said electrical device in the front of said streak camera tube with said front surface facing inward;
   f. means for transmitting said electrial pulses to said electrical device;

g. means for irradiating the entire front surface of said electrical device with said first beam part;

h. whereby electrons emitted therefrom an overlapping of said light and electrical pulses will travel down said streak tube be amplified, deflected and strike said phosphor screen, forming therein a streak image;

i. means for recording said streak image; and j. means for processing and displaying said recorded streak image.

* * * * *